United States Patent [19]

Johnston et al.

[11] 4,038,485
[45] July 26, 1977

[54] TEST COMPOSITION, DEVICE, AND METHOD

[75] Inventors: Katharine Gentry Johnston; Jerome Greyson, both of Elkhart, Ind.

[73] Assignee: Miles Laboratories, Inc., Elkart, Ind.

[21] Appl. No.: 724,365

[22] Filed: Sept. 17, 1976

Related U.S. Application Data

[63] Continuation-in-part of Ser. No. 667,981, March 18, 1976, abandoned.

[51] Int. Cl.$^2$ .................. G01N 31/22; G01N 33/16
[52] U.S. Cl. ....................... 23/230 B; 23/253 TP; 252/408
[58] Field of Search ............. 23/230 B, 253 TP; 252/408

[56] References Cited

U.S. PATENT DOCUMENTS 3,486,981 12/1969 Speck ........................... 252/408 X
3,867,518 2/1975 Coffey et al. ................. 23/230 B X
3,990,849 11/1976 Lee et al. ..................... 23/230 B Primary Examiner—Robert M. Reese
Attorney, Agent, or Firm—Edward H. Gorman, Jr.

[57] ABSTRACT

A test device, test composition, and method are disclosed for determining the presence of a component in a sample. The device comprises a carrier matrix incorporated with a reactant system which produces a detectable response upon contact with the sample component. After a predetermined time interval elapses, the production of the detectable response is terminated by an inhibitor system also incorporated with the matrix. The test composition comprises the reactant and inhibitor systems. The method of use comprises contacting the test device with a test sample suspected of containing the component, permitting a predetermined time to elapse after contacting, and observing any detectable response produced.

38 Claims, No Drawings

TEST COMPOSITION, DEVICE, AND METHOD

RELATED APPLICATION

This application is a Continuation-in-Part of Application Ser. No. 667,981, filed Mar. 18, 1976 and now abandoned.

BACKGROUND OF THE INVENTION

1. Field of the Invention

This invention relates to the analysis of a component in a test sample whereby a reactant system produces a detectable response upon contact with the component, and wherein the production of the detectable response ceases after a predetermined time period has elapsed.

2. Discussion of the Prior Art

The fields of diagnostic physics and chemistry have expanded at a phenomenal rate over the past 25 years such that, especially in the medical area, diagnosis of system parameters can be made with incredible facility and speed.

One such area of expansion has been that of medical diagnostics whereby numerous bodily functions can be studied merely by dipping a reagent-laden strip into a sample of bodily fluid, such as urine, and observing a detectable response such as a color appearance or change, or a change in the amount of light reflected from or absorbed by the strip.

Compatible with such "dip-and-read" methods have arisen numerous chemistries for detecting bodily fluid components. Most of these produce a detectable response which is quantitative or at least semi-quantitative. Thus, by measuring the response after a predetermined time, the analyst can obtain, not only a positive indication of the presence of a particular constituent in a bodily fluid, but also an estimate of how much of the constituent is present. Hence, such strips provide the physician with a facile diagnostic tool as well as the ability to gauge the extent of disease or bodily malfunction.

Illustrative of such strips currently in use are products available from the Ames Company Division of Miles Laboratories, Inc. under the trademarks CLINISTIX, MULTISTIX, KETOSTIX, N-MULTISTIX, DIASTIX, PHENISTIX, DEXTROSTIX, and others. Test devices such as these usually comprise one or more carrier matrices, such as absorbent paper, having respectively absorbed on them a particular reactant system which manifests a color change or appearance in the presence of a specific test sample component. Depending on the specific reactant system incorporated with a particular matrix, these devices can detect the presence of glucose, albumin, ketones, bilirubin, occult blood, nitrite, urobilinogen, hydrogen ion concentration (pH) or the like. The specific color appearance and its intensity observable within a specific time range after contacting the strip with the sample is indicative of the presence of a particular component and its concentration in the sample. Some of these test devices and their reactant systems are set forth in U.S. Pat. Nos. 3,123,443 (CLINISTIX); 3,212,855 (KETOSTOX); 3,814,668, 3,164,534 and 2,981,606 (DIASTIX); and 3,092,465, 3,298,789, 3,164,534 and 2,981,606 (DEXTROSTIX).

Typically, diagnostic reagent tests, such as "dip-and-read" reagent strips are accompanied by detailed printed instructions which must be carefully followed to assure accuracy. In the case where the detectable response is a color change, particular care is required. A chart of varying colors for comparison with the strip is provided, and, since in most cases the quantitativeness of the device is dependent upon determining the degree of color formation with respect to time, it is imperative that the color change be compared with the chart within a prescribed time range after dipping into the sample. Waiting periods must be accurately adhered to - too early a reading resulting in too little color formation, and too late a reading resulting in too intense a color formation or even the occurance of an ancillary, intervening color. Hence, if the color formation is compared with the color chart too early or too late, an inaccurate result can be, and often is, obtained.

In an attempt to eliminate the criticality of accurate timing in reading, which is both inconvenient and potentially inaccurate, an extensive research program was engaged in to find a way of precluding the necessity of timing the reading of prior art test devices. Primarily, a way was sought whereby the production of a detectable response would automatically be terminated after a predetermined time, and where the response would remain constant for relatively long storage periods. Thus, color chart comparison could be made at the convenience of the user, or at a time remote from the actual contacting of the device with the sample. For a long time there has been a consensus of opinion in the art of diagnostic reagent chemistry that such test devices would dramatically enhance the state of the art. Yet, to date none has been proposed which would successfully provide the long-awaited solution. None, that is, until the discovery of the present invention.

SUMMARY OF THE INVENTION

Briefly stated, the present invention relates to a test composition, test device and method for its preparation, and method for determining the presence of a component in a sample. The composition comprises a reactant system which interacts with the component upon contact to produce a detectable response, and an inhibitor system which, upon contact with the sample, prevents the reactant system from interacting further with the component after a predetermined time has elapsed. The test device comprises a carrier matrix incorporated with the test composition. The method for determining the presence of a component in a sample comprises contacting a test sample suspected of containing the component with a carrier matrix incorporated with the test composition, incubating the matrix containing the composition and test sample for a predetermined time, and observing a detectable response.

DETAILED DESCRIPTION OF THE INVENTION

The present invention embodies many forms of diagnostic chemistry including known reactant systems presently in use such as pH and other ion concentration indicators, and more complex reagent systems such as those used for determining bodily fluid components. These are ideally suited for and compatible with the concepts presently disclosed. Hence prior art diagnostic test devices for occult blood, glucose, bilirubin, blood urea nitrogen, bacteriurea, urobilinogen, cholesterol, protein, and others may all be modified in accordance with the teachings herein.

The present invention resides in advantageously utilizing known or novel reactant systems such that the interaction between the sample component and the reactant system ceases to occur after a predetermined time interval. Thus it is seen that the quantum of detectable response is fixed for any given reactant system: a color formed in the interaction neither increases nor fades; the amount of an ultraviolet light-sensitive product formed or used up from the interaction remains constant.

The presently-described effects can be achieved in numerous ways. A preferred way is to provide an inhibitor system which physically prevents further interaction by forming a gel, polymer or hardened surface, thereby precluding physical contact between the reactant system and the component after the predetermined time interval has elapsed.

Another way is to provide the test composition with an inhibitor system which deactivates the reactant system. Thus, in the case where a heat-labile enzyme is critical to the functioning of the reactant system, the inhibitor system can take the form of a heat-generating agent which raises the temperature of the test composition to the point where the enzyme becomes deactivated after the predetermined time interval has elapsed.

Still another way is to provide an inhibitor system which poisons or chemically interferes with one or more components of the reactant system, thereby suppressing interaction with the sample component after the predetermined time. These and other inhibitor systems are within the scope of the present invention, the crucial factor being the ability of the inhibitor system to permit interaction between the reactant system and the component at the time of contact between the sample and the test composition, but to preclude such interaction at some later, preset time.

Where an inhibitor system which physically prevents reactant system/component interaction, i.e., an inhibitor system which hardens or gels, is desired, there are many routes available. Among the gelling or hardenable materials employable are those which are rapidly reactive at room temperature and which begin reacting, or are initiated upon contact with the test sample. These inhibitor compositions must harden or gel at a rate sufficient to inhibit production of detectable response after a relatively short elapse of time. Equally desirable is that the gelled or hardened inhibitor deter or prevent further changes in color or other dissipation of the detectable response.

Typical of such inhibitor systems are polymerizable or crosslinkable water-soluble polymers, epoxide/polyamine mixtures, water-reactive polyisocyanates, hydroxyl ionpolymerizable acrylate and substituted acrylate esters, polyvinyl alcohol mixtures with various metal compounds {e.g. borates, vanadates, Cr (III), and Ti (IV)}, sodium carboxymethyl cellulose and Al (III), polyvinyl alcohol mixtures with polyphenolic compounds (e.g. resorcinol, catechol, phloroglucinol, and dyes and diazonium salts), a mixture of polyvinyl alcohol and dimethylolurea with ammonium chloride catalyst, dimethylolurea mixtures with hydroxyalkylcellulose and hydrolyzed maleic anhydride copolymers or polyacrylic acid, polyvinyl alcohol/polyaldehydic compound mixtures, polyvinylpyrrolidone complexes (i.e. with substances such as polycarboxylic acids, a methyl vinylether/maleic anhydride copolymer available from GAF Corporation, or a polyacrylic acid), acidic copolymer/polyethylene glycol mixtures, and polyvinyl alcohol mixtures with precipitating agents (e.g. $Na_2CO_3$, $Na_2SO_4$ or $K_2SO_4$).

Delay in polymerization or crosslinking of the water soluble polymer, can be achieved by isolating the initiators from the water-soluble polymer until the test composition has been contacted by the test sample. One way to achieve such separation of polymer and initiator is to encapsulate the initiator in water-soluble microcapsules or in microcapsules which rupture upon wetting. Hence gelatin microcapsules containing the initiator would dissolve upon contact with an aqueous test sample, thereby freeing the initiator to further polymerize the water-soluble polymer.

Microcapsules which rupture upon wetting comprise osmotically fragile, semipermeable, membranous walls which encapsulate an aqueous phase containing the initiator. The aqueous phase is of a relatively high specific gravity with respect to the test sample. When the capsules are contacted by the test sample, an osmotic gradient occurs across the membrane which causes an increase in pressure within the capsule sufficient to rupture its walls, thus releasing the initiator.

Physical inhibition by separating the reactant system from the component can also be achieved with an inhibitor system comprising an epoxide and deactivated polyamine source which yields available polyamines on contact with water. Typical of such polyamine sources are ketimines and molecular sieves impregnated with a polyamine. In the former case, the ketimine reacts with water to form polyamine and a ketone. In the latter case, water is capable of entering the molecular sieve lattice and displacing the polyamine.

Alternatively, the test composition can be incorporated with a water-foamable polyisocyanate such as Hypol, available from the Dewey and Almy Chemical Division of W. R. Grace & Co.

Of the base, or hydroxyl ion-catalyzed acrylate inhibitor systems, 2-cyanoacrylate esters are especially suited to the present invention. These esters are essential components in adhesives manufactured by the Eastman Kodak Company, and are rapidly polymerizable in the presence of water to yield hard polymers. The methyl- and ethyl- esters are those which are primarily available in commercial adhesive formulations, such as from Kodak, the adhesives containing stabilizers and thickeners in addition to the esters. Methyl-2-cyanoacrylate is contained in Eastman 910, and ethyl-2-cyanoacrylate is the primary ester in Eastman 910 EM.

Polyvinyl alcohol, when mixed with boric acid, gels rapidly in the presence of alkali, such as sodium hydroxide, and is therefore suitable as an inhibitor system. A preferred method of utilizing this alternative is to incorporate the alkali into the test composition in the form of water-soluble or osmotically fragile microcapsules. Thus, when contacted with test sample, all the reagents of the inhibitor system are combined and the formation of a gel stops the analysis.

Besides being useful with borax (boric acid and alkali), polyvinyl alcohol also gels with a variety of other metal ions and salts, among these being vanadates, trivalent chromium and tetravalent titanium. For example, potassium titanium oxalate $\{TiO(C_2O_4K)_2 \cdot 2H_2O\}$ and other organic titanates rapidly insolubilize polyvinyl alcohol at room temperature at a pH of above about 7. Additionally, polyvinyl alcohol forms thermally reversible gels with polyphenolic compounds such as resorcinol, catechol, phloroglucinol and certain dyes and diazonium salts.

Polyvinyl alcohol is additionally useful in the present invention through its ability to cross-link via acetal formation with 1,3-bishydroxymethylurea (dimethylolurea) and related compounds in the presence of ammonium chloride. As in many of the foregoing systems, the catalyst or initiator ($NH_4Cl$) can be isolated by means such as microencapsulation.

Polyfunctional aldehydes also react with polyvinyl alcohol to form acetal cross linking groups. In this technique an acid catalyst, such as oxalic acid or other acid compatible with the reactant system is incorporated into the test composition and the aldehyde is isolated from the polyvinylalcohol such as by microencapsulation. Of course, the acid can be isolated in lieu of the aldehyde, provided the latter is sufficiently unreactive towards polyvinyl alcohol absent the catalyst.

Polymeric precipitates have been found useful in the present invention as the inhibitor system. These are exemplified by the precipitation of polyvinyl alcohol from solution by salts such as $Na_2CO_3$, $Na_2SO_4$ and $K_2SO_4$. Moreover, polymeric acids such as polyacrylic acid can be precipitated from solution or gelled by acetate salts of heavy metals or other water-soluble sources of divalent ions, as well as by polyethylene glycol.

Hydroxypropyl cellulose (KLUCEL, available from Hercules, Inc.) is another polymer which lends itself to the inhibitor system of the present test composition. This material can be cross linked with acidic polymers such as hydrolyzed maleic anhydride copolymers or polyacrylic acid through the use of compounds such as dimethylolurea, preferably in the presence of low pH.

Another gelation system useful in the test composition is sodium carboxymethyl cellulose and Al(III) ion.

GANTREZAN, a methylvinylether/maleic anhydride copolymer available from GAF Corporation, is applicable to the test composition in several ways. It forms an insoluble complex with polyvinylpyrrolidone at a pH less than about 5. Polyacrylic acid behaves similarly to GANTREZAN with polyvinylpyrrolidone. GANTREZAN also forms an insoluble complex with gelatin in acidic solution. Likewise, GANTREZAN and other acid polymers and copolymers are precipitated by compounds such as glycols, polyvinyl alcohol, hydroxyalkylcellulose and diamines.

As stated above, other inhibitor systems are well within the purview of the present invention. Thus, an inhibitor system can be employed other than those which physically separate the reactant system and the analysate component. For example, an enzyme which is heat-labile will not function in a reactant system if the temperature of the system becomes sufficiently high to deactivate it. Accordingly, a test composition such an enzyme can be precluded from producing a detectable response after a predetermined time by use of a heat-generating inhibitor system.

Similarly, the inhibitor system can comprise a reactant system poison. For example, enzymes containing mercaptogroups (-SH) are deactivated by Hg(II), and enzymes in general are deactivated in the presence of strong acids and bases such as HCl and NaOH. Examples of enzymes which are inhibited by Hg(II) are glutamate decarboxylase, lactate dehydrogenase, malate dehydrogenase, myokinase, alkaline phosphatase, acid phosphatase (pH 5.2), aldehyde oxidase, diamino acid oxidase, $\beta$-amylase, carbonic anhydrase, cholinesterase, $\alpha$-glucosidase, $\beta$-glucuronidase, homogentisate oxidase, 3-hydroxyanthranilate oxidase, and invertase. Thus the present invention encompasses incorporating such inhibitor systems into the test composition.

Heat-labile enzymes such as salicylate hydroxylase are equally within the scope of the present invention. Materials which produce heat upon contact with an aqueous test sample include NaOH, $AlCl_3$, $TiCl_3$, Aluminum alkyls and others.

A way of delaying the denaturing or poisoning of an enzyme is to isolate the heat-producing or poisonous inhibitor system with microcapsules. Thus, water soluble encapsulation materials can be chosen such that the heat producing materials are not exposed to the sample until after the encapsulation material has dissolved. Water-soluble materials such as gelatin, acrylamides, styrene/maleic acid copolymers and hydroxypropyl cellulose and mixtures such as a coacervate of gelatin and natural or synthetic polymers are suitable for encapsulation.

As is stated supra, microcapsules of varying kind lend themselves especially well to the present invention when ingredients must be temporarily separated. They can be prepared by a variety of well-known methods. Indicative of these is the method described in Angew. Chem. Internat. Edit., 14:539 (1975) and the references cited therein. Techniques such as interfacial polycondensation, coacervation and the like will produce microcapsules. Other techniques such as centrifugation, spray drying, and other physico-mechanical techniques will likewise find utility in preparing the microcapsules.

Interfacial polycondensation is a preferred method for making the microcapsules because of the relative ease it provides. In this technique two reactive species (comonomers or oligomers) are caused to react at the interface of a multiphase system. There, polycondensation occurs, forming a thin polymeric film which is insoluble in the media containing the monomers. Suitable microcapsules of the osmotically fragile type have been prepared by dissolving a first comonomer component, such as a polyfunctional amine, in an aqueous phase containing the substance to be isolated. This aqueous phase is preferably one with a high specific gravity or osmolality relative to the expected osmolality range of the sample to be analyzed. This aqueous phase is then dispersed or emulsified in a water immiscible phase such as mineral oil. A second comonomer, such as a polyfunctional acyl halide, is then added to the suspension or emulsion. When the comonomers are polyfunctional amines and acyl halides, polyamide microcapsules are formed, each of which contains a portion of the aqueous phase, i.e. the isolated substance.

Suitable polymeric material useful to form the osmotically fragile, semipermeable membrane wall of the microcapsules include, in addition to polyamide, polyester, polyurethane, polyurea, and the like.

Another way of separating ingredients of the inhibitor system, where one of the ingredients is soluble in water and the other in organic solvents, is to utilize a "two-dip" process. Thus the carrier matrix of a test device is first incorporated with an aqueous solution of one ingredient, dried, and subsequently incorporated with a second solution of the other ingredient in an organic solvent.

In some of the inhibitor systems described above, not requiring ingredient isolation, such as those utilizing 2-cyanoacrylates, water-foamable isocyanates, and epoxide reagents, care must be taken to exclude moisture, both during preparation of the test composition and device, and upon storage prior to ultimate use. Thus polymerization of the inhibitor system is precluded until contact with the test sample.

Gelling or hardening inhibitor systems, typified by certain of those mentioned above, together with a desired reactant system, can be incorporated with a carrier matrix by any suitable means to produce the test device of the present invention. Thus a carrier matrix can be dipped in a single solution of all the ingredients of the reactant and inhibitor systems. Alternatively, where a "two-dip" method is required because of the necessity of isolating ingredients, the matrix is alternately dipped, dried, and redipped as described above. In the case where microcapsules are employed, they can be affixed to the matrix through the use of binders. Among those found to be particularly desirable are cellulose acetate, cellulose acetate butyrate, hydroxy propyl cellulose and polyvinylpyrrolidone. Binders should be immiscible with the test sample and permit the sample to be absorbed into the carrier matrix.

Suitable materials which may be used as the carrier matrix of the test device include paper, cellulose, wood, synthetic resin fleeces, glass fiber and other synthetic papers, polypropylene felt, non-woven and woven fabrics, and the like. The matrix is advantageously affixed by any suitable means to a conventional carrier member, such as a polymer strip, to facilitate use.

In the method of using the test device, the matrix having incorporated therewith the reactant and inhibitor systems is immersed in the test sample. The predetermined time interval appropriate to the device is permitted to elapse, and the device is then analyzed for the detectable response. Where the response is color formation or change, the device can be compared with a standard color chart. Should the response comprise a change in light reflectance, the device is examined in an appropriate light-measuring instrument such as those well-known in the art.

The following examples are provided to further illustrate and clarify the present invention. It is to be understood however, that these only serve to exemplify presently preferred embodiments, and are in no way to be interpreted as limiting the scope of the invention.

EXAMPLE I

A ten percent by weight solution in chloroform of Eastman 910 adhesive containing methyl 2-cyanoacrylate (Eastman Chemical Products, Inc., Kingsport, Tennessee, a subsidiary of Eastman Kodak Company), was prepared and stored in a tightly capped glass container. A test device for detecting glucose in urine (similar to CLINISTIX) was prepared in the following manner. Whatman 3MM filter papers were impregnated with a test reagent solution as illustrated in U.S. Pat. Nos. 2,981,606 and 3,154,534 and then dried. Specifically, the formulation was as follows:

| CLINISTIX Formulation | | |
| --- | --- | --- |
| Distilled Water | 758.1 | ml |
| Ethanol-95% | 205.0 | ml |
| Carageenan Viscarin, manufactured by Marine Colloids, Inc. | 2.5 | g. |
| Polyvinylpyrrollidone | 25.0 | g. |
| Dyes (FD&C 3&4) | 0.29 | g. |
| 0-Tolidine · 2HCl | 5.0 | g. |
| Citric acid (Anhyd.) | 15.42 | g. |
| Sodium citrate | 67.92 | g. |
| GANTREZ AN-139 | 7.5 | g. |
| Surfactant | 2.5 | g. |
| Glucose oxidase | 76.0 | ml |
| Peroxidase | 0.5 | g. |

Portions of this impregnated paper were then further impregnated with the above described solutions. Others were treated with chloroform only, as a control. The impregnation vessel permitted the paper to enter and exit, but was covered to reduce evaporation of the chloroform, while allowing excess impregnating solution to drain from the paper in a solvent-rich atmosphere within the vessel. After removal of the paper from the bath, solvent was allowed to evaporate for 10 to 30 minutes at ambient temperature in an atmosphere of controlled low humidity ($<10\%RH$). The monomer-impregnated paper was stored in the dark, dry atmosphere and subsequently mounted on plastic backing and slit into the usual reagent strip format. The prepared strips were then stored in dark glass bottles in the presence of silica gel moisture adsorbent.

The strips thus produced were evaluated by dipping them individually for 3 seconds into urine samples of known glucose concentration (0, 50, 100, 200, and 500 mg/dl), removing excess sample, and introducing them into a reflectance measuring apparatus. Reflectance readings at 680 nm were recorded as a function of time from $t = 15$ seconds including dip time for 3.5 minutes. In Table I changes in reflectance values at intervals and final reflectance values are shown for the glucose-specific paper impregnated with 10% Eastman 910 at the several glucose concentrations. The change in reflectance at 15 sec. is the difference from the reflectance value when no glucose is present. It is apparent that no change in reflectance value is observed after 2 minutes. These final colors may be clearly differentiated visually and continue to remain stable for periods of several days to several weeks depending upon storage conditions.

The test strips which were only impregnated with chloroform (controls) developed very intense colors 10 seconds after dipping, but color development continued rapidly, and after two minutes the strips were black and no differentiation could be made.

TABLE 1

CHANGE IN REFLECTANCE WITH TIME AFTER SAMPLE CONTACT

| Glucose Concentration (mg %) | 15 sec Δ % R * | 40 sec Δ % R + | 65 sec Δ % R + | 90 sec Δ % R + | 115 sec Δ % R + | 140 sec Δ % R + | 165 sec Δ % R + | 215 sec Δ % R + | FINAL % R |
| --- | --- | --- | --- | --- | --- | --- | --- | --- | --- |
| 50 | 6.8 | 8.5 | 3.5 | 0.1 | 0 | 0 | 0 | 0 | 59. |
| 100 | 13.8 | 13.8 | 5.6 | 2.0 | 0.1 | 0 | 0 | 0 | 43. |
| 200 | 22.6 | 15.3 | 6.2 | 2.7 | 0.7 | 0 | 0 | 0 | 31. |
| 500 | 30.8 | 15.7 | 6.5 | 2.7 | 0.7 | 0 | 0 | 0 | 22. |

\* %R at t = 15 sec. = %R$_{(0\ mg\%\ glucose)}$ -%R$_{(n\ mg\%\ glucose)}$
+ %R at $t$ =t sec = %R$_{(preceding\ t)}$-%R$_{(t)}$

EXAMPLE II

Previously prepared glucose-sensitive reagent paper was impregnated as in Example I with a chloroform solution containing 10% by weight Eastman 910 EM (ethyl-2-cyano-acrylate) 1% (w/v solid non-ionic detergent, and 0.01% (w/v) solid dicarboxylic acid. Strips prepared from this impregnated paper exhibited characteristics similar to those of Example I and the colored reacted strips exhibited a particularly smooth uniform appearance.

EXAMPLE III

Ketone-sensitive reagent paper was prepared, in accordance with U.S. Pat. No. 3,202,855 by immersing Whatman 3MM filter papers in the following First Dip mixture, drying, and subsequently immersion in the Second Dip.

| First Dip | | |
|---|---|---|
| $H_2O$ | 722 | ml |
| Sodium Phosphate Tribasic | 202.2 | g. |
| Sodium Phosphate Dibasic (Anhyd.) | 86.7 | g. |
| Aminoacetic Acid | 180.6 | g. |
| Second Dip | | |
| Surfactants | 1.64 | g. |
| Polyvinylpyrrolidone/vinyl-acetate copolymer E-535 | 67 | ml |
| Sodium Nitroferricyanide | 8.24 | g. |
| Dimethyl sulfoxide | 401 | ml |
| Chloroform | 350 | ml |
| Ethanol, Anhydrous | 200 | ml |

Strips thus prepared were then impregnated with a chloroform solution containing 10% by weight of Eastman 910 EM as in Example I. Strips prepared from this impregnated paper and evaluated with urines containing several concentrations of acetoacetic acid exhibited excellent characteristics of color development, and the color intensities indicative of acetoacetic acid concentration of the urine tested remained stable.

EXAMPLE IV

Glucose-sensitive reagent paper was impregnated with a benzene solution of 10% Eastman 910, containing methyl 2-cyanoacrylate. Upon evaluation, strips of this paper exhibited the excellent properties of the previous Examples.

EXAMPLE V

A "one-dip" system was prepared from the following formulation.

| Reagent A | | |
|---|---|---|
| Sodium phosphate, tribasic | 2.02 | g |
| Sodium phosphate dibasic anhydrous | 0.87 | g |
| Glycine (aminoacetic acid) | 1.81 | g |
| Sodium nitroferricyanide (milled and dried) | 82.4 | mg |
| Reagent B | | |
| Dioctyl sodium sulfosuccinate | 8.4 | mg |
| GAFAC Surfactant RE-610 (Available from GAF Corp.) | 8.0 | mg |
| Chloroform | 16.7 | ml |
| Hypol 2000 (polyurethane pre-polymer) Mix until in solution | 0.9 | g |

All of the constituents in "Reagent A" were ground in a mortar and pestle to a fine powder and suspended in "Reagent B". Dry Whatman 3MM filter paper (available from the 3M Co., St. Paul, Minn.) was impregnated with this suspension, and strips prepared from this impregnated paper were evaluated with urines containing several different concentrations of acetoacetic acid. The color intensities of the reacted strips were stable and were a function of acetoacetic acid concentration of the urine tested.

EXAMPLE VI

A glucose indicator reagent and an enzyme solution, having the following compositions, were prepared:

| Glucose Indicator Reagent | | |
|---|---|---|
| Distilled water | 16.6 | ml |
| Polyvinylpyrrolidone (PVP) | 9.5 | ml |
| Potassium iodide | 1.5 | g |
| FD&C Blue No. 1 | 5.3 | mg |
| Citric Acid | 0.497 | g |
| Trisodium Citrate | 2.182 | g |
| (Ethylenedinitrilo)-tetracetic acid tetrasodium salt | 1.67 | g |
| GANTREZ AN, 10% solution | 5 | ml |
| Enzyme solution | 16.7 | ml |
| Enzyme Solution | | |
| 225 ml. glucose oxidase | | |
| 0.842 g. peroxidase | | |

All of the foregoing reagents were mixed until they were in solution. Equal volumes of this reagent indicator solution, urine containing glucose, and Hypol 2000 were added to a spot plate impression and mixed with a spatula until foaming began (about 1 minute). The prepolymer formed a colored solid foam in 3 to 5 minutes.

The system, when evaluated with urine containing 0, 100, 250, 500, 1,000, and 2,000 mg glucose/dl developed stable color after a short time, and the color intensities were indicative of the concentration of glucose. The final colors ranged from blue, to green, to brown depending upon glucose concentration, and were compared to color standards.

Since one drop of Hypol 2000 forms enough foam to fill the spot plate impression, the test can be run on one drop of urine sample and still be read visually.

EXAMPLE VII

Ketone-specific reagent paper prepared in accordance with U.S. Pat. No. 3,212,855 was impregnated with a 10% chloroform solution of Hypol 2000, a water-foamable urethane prepolymer available from Dewey and Almy Chemical Division of W. R. Grace Co. This solution may contain, in addition, any one of several ionic detergents in a concentration varying between 1 and 5% of the prepolymer weight. Strips prepared with this impregnated paper were evaluated with urines containing different amounts of acetoacetic acid and attained final color intensities within 2 to 4 minutes. These color intensities were stable and were a clearly visually distinguishable function of acetoacetic acid concentration.

From the foregoing it is clear that incorporation of the concepts of the present invention is applicable, not only to the production of test strips or devices of the dip-and-read type, but to other forms of tests as well, including those in the form of liquid systems.

EXAMPLE VIII

A test device for the determination of urobilinogen in urine was prepared by first impregnating Whatman 3MM filter paper with the following mixture:

| Distilled water | 70.5 | g. |
|---|---|---|
| GANTREZ AN-139 | 5.6 | g. |
| Sulfasalicylic Acid | 9.16 | g. |
| Caffeine | 7.05 | g. |
| Sulfamic Acid | 1.41 | g. |
| p-Dimethylaminobenzaldehyde | 0.53 | g. |

-continued

| | | |
|---|---|---|
| (Ethylenedinitrilo)-tetracetic acid tetrasodium salt | 0.14 | g. |
| Ascorbic Acid | 3.52 | g. |
| Sodium lauryl sulfate | 0.70 | g. |

The paper was then dried and further impregnated with a 4% by weight solution of polyvinylpyrrolidone in chloroform. The resultant paper was then dried and mounted on polystyrene strips for testing. The reagent strips were evaluated by dipping them for three seconds into urine samples of known urobilinogen concentrations (0, 4, 8, and 12 Ehrlich units). The colors developed within two minutes and were found to be indicative of urobilinogen concentration. This time-ingredient effect is achieved by the rapid complex formation of hydrolyzed methyl vinyl ether/maleic anhydride copolymer with polyvinylpyrrolidone at low pH.

EXAMPLE IX

A strip used for the detection of occult blood in urine was prepared by impregnating Whatman 3MM filter paper with the following solution:

| | | |
|---|---|---|
| Sodium lauryl sulfate | 0.84 | g. |
| Cumene hydroperoxide | 1.67 | g. |
| 6-Methoxyquinoline | 0.39 | g. |
| Sodium Citrate . 2H$_2$O | 1.79 | g. |
| Citric Acid | 2.32 | g. |
| 3,3',5,5'-tetramethylbenzidine | 0.45 | g. |
| Triethyanolamine borate | 5.58 | g. |
| (Ethylenedinitrilo) tetracetic acid, tetra sodium salt | 0.06 | g. |
| Dimethyl sulfone | 5.58 | g. |
| Water | 40.67 | g. |
| Dimethylformide | 40.67 | g. |

After being dried, the paper was further impregnated with a 1% by weight solution of Eastman 910EM in chloroform. The strips prepared from this paper upon evaluation in urine samples containing known quantities of hemoglobin (0, 0.016, 0.064, 0.16, 0.80 mg/dl) produced within two minutes remarkably stable colors, the intensity of which was a function of hemoglobin concentration.

What is claimed is:

1. A test composition for detecting the presence of a component in a sample comprising
    a. a reactant system which, upon contact with said sample, interacts with said component to produce a detectable response, and
    b. an inhibitor system which, upon contact with said sample, prevents said reactant system from interacting with said component after elapse of a predetermined time.

2. The test composition of claim 1 in which said detectable response is a color change.

3. The test composition of claim 1 in which said inhibitor system comprises an ester of 2-cyanoacrylic acid.

4. The test composition of claim 1 in which said inhibitor system comprises polyvinyl alcohol.

5. The test composition of claim 1 in which said component is glucose, ketone, occult blood, bilirubin, urobilinogen, cholesterol, hydrogen ion, protein or nitrite.

6. The test composition of claim 1 in which the rate of production of said detectable response is dependent upon the amount of said component in said sample.

7. The test composition of claim 1 in which said inhibitor system terminates the production of the detectable response by undergoing a hardening or gelling reaction in competition with production of said response.

8. The test composition of claim 1 in which said inhibitor system contains a substance capable of producing heat upon contact with said sample, thereby elevating the temperature after a predetermined time, such that said reactant system is prevented from interacting with said component.

9. The test composition of claim 1 in which said inhibitor system is a poison for said reactant system after a predetermined time, thereby preventing said reactant system from interacting with said component.

10. The test composition of claim 1 in which said inhibitor system comprises a water-reactive polyisocyanate.

11. The test composition of claim 1 in which said inhibitor system comprises a material which gels or hardens on contact with said sample.

12. The test composition of claim 11 in which said material hardens or gels at a rate sufficient to inhibit further interaction between said reactant system and said component.

13. The test composition of claim 11 in which the gelling or hardening is initiated upon contact with water.

14. A test device for detecting the presence of a component in a sample comprising a carrier matrix incorporated with
    a. a reactant system which, upon contact with said sample, interacts with said component to produce a detectable response, and
    b. an inhibitor system which, upon contact with the sample, prevents the reactant system from interacting with the component after elapse of a predetermined time.

15. The test device of claim 14 in which said inhibitor system is capable of producing heat upon contact with said sample, thereby elevating the temperature of said device, after a predetermined time, such that said reactant system is prevented from interacting with said component.

16. The test device of claim 14 in which said inhibitor system is capable of poisoning said reactant system after a predetermined time, thereby preventing said reactant system from interacting with said component.

17. The test device of claim 14 in which the component is glucose, ketone, occult blood, bilirubin, urobilinogen, cholesterol, hydrogenion, protein, or nitrite.

18. The test device of claim 14 in which said detectable response is a color change.

19. The test device of claim 14 in which the rate of production of said detectable response is dependent on the amount of said component in said sample.

20. The test device of claim 14 in which said inhibitor system comprises a material which hardens or gels on contact with said sample.

21. The test device of claim 20 in which said material gels or hardens at a rate sufficient to inhibit production of said detectable response after a predetermined time.

22. The test device of claim 20 in which said material is 2-cyanoacrylic acid or an ester thereof.

23. The test device of claim 20 in which said material comprises polyvinyl alcohol.

24. The test device of claim 20 in which the gelling or hardening of said material is initiated upon contact with water.

25. The test device of claim 20 in which said material is a water-reactive polyisocyanate.

26. A method for detecting the presence of a component in a sample, the method comprising;
   a. contacting said sample with a carrier matrix incorporated with (i) a reactant system which, upon contact with said sample, interacts with said component to produce a detectable response, and (ii) an inhibitor system which, upon contact with said sample, prevents the reactant system from interacting with the component after a predetermined time,
   b. incubating the matrix, after contact with the said sample, for said predetermined time, and
   c. observing said detectable response.

27. The method of claim 26 in which said inhibitor system produces heat upon contact with said sample, thereby elevating the temperature of said matrix, after a predetermined time, such that the reactant system is prevented from interacting with said component.

28. The method of claim 26 in which said inhibitor system is capable of poisoning said reactant system after a predetermined time.

29. The method of claim 26 in which said component is glucose, ketone, occult blood, bilirubin, urobilinogen, cholesterol, hydrogen ion, protein, or nitrite.

30. The method of claim 26 in which said inhibitor system is a material which hardens or gels upon contact with said sample.

31. The method of claim 30 in which said material is 2-cyanoacrylic acid or an ester thereof.

32. The method of claim 30 in which said material is polyvinyl alcohol.

33. A method for producing a test device for detecting the presence of a component in a sample which comprises incorporating a carrier matrix with
   a. a reactant system which, when contacted with said sample containing said component, interacts therewith to produce a detectable response, and
   b. an inhibitor system which, on contact with said sample, prevents said reactant system from interacting with said component after a predetermined time.

34. The method of claim 33 wherein the rate of production of said detectable response is dependent upon the amount of said component in said sample.

35. The method of claim 33 in which said inhibitor system comprises a material which gels or hardens on contact with said sample.

36. The method of claim 33 in which said reactant and inhibitor systems are incorporated with said carrier sequentially.

37. A method for producing a test device comprising incorporating with a carrier matrix having incorporated therewith a reactant system which, upon contacted with a sample containing a component whose presence is to be detected, interacts therewith to produce a color-change; an inhibitor system which, on contact with said sample, prevents said color-change production after a predetermined time.

38. The method of claim 37 in which the rate of said color-change production is dependent upon the amount of said component in said sample.

* * * * *

UNITED STATES PATENT OFFICE
CERTIFICATE OF CORRECTION

Patent No. 4,038,485              Dated July 26, 1977

Inventor(s) Katharine Gentry Johnston et al.

It is certified that error appears in the above-identified patent and that said Letters Patent are hereby corrected as shown below:

Column 5, lines 31, 36, 37, 38 and 39, "GANTREZAN", each occurrence, should read -- GANTREZ AN --.

Column 9, line 1, "(ethyl-2-cyano-acrylate)" and "(w/v" should read -- (ethyl-2-cyanoacrylate) --; and -- (w/v) --, respectively.

Signed and Sealed this

Twenty-seventh Day of December 1977

[SEAL]

Attest:

RUTH C. MASON  
Attesting Officer

LUTRELLE F. PARKER  
Acting Commissioner of Patents and Trademarks